United States Patent
Chang et al.

(10) Patent No.: US 9,833,473 B2
(45) Date of Patent: Dec. 5, 2017

(54) TOLEROGENIC DENDRITIC CELLS FOR TREATING MYOCARDIAL INFARCTION AND MANUFACTURING METHOD THEREOF

(71) Applicant: THE CATHOLIC UNIVERSITY OF KOREA INDUSTRY-ACADEMIC COOPERATION FOUNDATION, Seoul (KR)

(72) Inventors: Ki-Yuk Chang, Seoul (KR); Eun-Ho Choo, Seoul (KR); Hyo-Eun Park, Gwangmyeong-si (KR); Eun-Hye Park, Yongin-si (KR); Dae-Seog Lim, Seongnam-si (KR); Jun-Ho Lee, Seongnam-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/508,842

(22) Filed: Oct. 7, 2014

(65) Prior Publication Data

US 2016/0095882 A1   Apr. 7, 2016

(51) Int. Cl.
*A61K 35/15*   (2015.01)
*C12N 5/0784*   (2010.01)
*A61K 35/12*   (2015.01)

(52) U.S. Cl.
CPC ............ *A61K 35/15* (2013.01); *C12N 5/0639* (2013.01); *A61K 2035/124* (2013.01); *C12N 2500/84* (2013.01); *C12N 2501/052* (2013.01); *C12N 2501/22* (2013.01); *C12N 2501/25* (2013.01); *C12N 2501/998* (2013.01)

(58) Field of Classification Search
None
See application file for complete search history.

(56) References Cited

U.S. PATENT DOCUMENTS

2010/0203067 A1* 8/2010 Spencer ............... C12N 5/0639
424/184.1

OTHER PUBLICATIONS

Hermansson et al., Immunotherapy With Tolerogenic Apolipoprotein B-100-Loaded Dendritic Cells Attenuates Atherosclerosis in Hypercholesterolemic Mice, Cicrulation 2011; 123: 1083-1091.*
Anzai et al., Regulatory Role of Dendritic Cells in Postinfarction Healing and Left Ventricular Remodeling, Circulation Mar. 13, 2012; 125(10): 1234-1245.*
Fujii et al., The Linkage of Innate to Adaptive Immunity via Maturing Dendritic cells in Vivo Requires CD40 Ligation in Addition to Antigen Presentation and CD80/86 Costimulation, J. Exp. Med. vol. 199, No. 12, Jun. 21, 2004.*

* cited by examiner

*Primary Examiner* — Suzanne M Noakes
*Assistant Examiner* — Stephen Chong
(74) *Attorney, Agent, or Firm* — JHK Law; Joseph Hyosuk Kim

(57) ABSTRACT

Provided are the tolerogenic dendritic cells for treating a myocardial infarction and a method for preparing the same, and more particularly, the tolerogenic dendritic cells for treating a myocardial infarction, which can treat cardiac insufficiency that occurs by excessive remodeling of left ventricle in the heart muscle recovery process after an acute myocardial infarction, and a method for preparing the tolergenic dendritic cells. According to the present invention, the inflammatory reaction and the excessive remodeling of left ventricle in the heart muscle recovery process after a myocardial infarction can be inhibited, and thus, the incidence rate of cardiac insufficiency can be significantly reduced, thereby being effectively used for treating a myocardial infarction.

2 Claims, 7 Drawing Sheets

FIG. 3A - Heart extract treatment

FIG. 3B - Serum treatment

FIG. 4

|  |  | H&E | Masson Trichrome | CD3 | MAC |
|---|---|---|---|---|---|
| 4W | OP-con |  |  |  |  |
|  | 2X10^5 |  |  |  |  |
|  | 1X10^6 |  |  |  |  |

TOLEROGENIC DENDRITIC CELLS FOR TREATING MYOCARDIAL INFARCTION AND MANUFACTURING METHOD THEREOF

TECHNICAL FIELD

The present invention relates to the tolerogenic dendritic cells for treating a myocardial infarction, and a method for preparing the same, and more particularly, to the tolerogenic dendritic cells for treating a myocardial infarction, which can treat cardiac insufficiency that occurs by excessive remodeling of left ventricle in the heart muscle recovery process after an acute myocardial infarction, and a method for preparing the tolergenic dendritic cells.

BACKGROUND

The dendritic cells principally are kind of special antigen-presenting cells performing the function of presenting antigen to a T cell, and present in a type of a spatial dendrite in a lymphatic gland, a spleen, the thymus, under the skin, or the intercellular spaces of various tissues. The dendritic cells play an important role in activating T cells by presenting various antigen samples along with MHC (major histocompatibility complex) Class I or MHC Class II complex to a T cell by absorbing an antigen in cells.

The dendritic cells are differentiated in a state of different maturities according to a type of environmental signal present around the cells, and thus, exist as immature, semi-mature, or mature dendritic cells. The immature dendritic cells are discovered at an initial maturity state and perform a primary function collecting and removing debris from transcellular fluid. However, the immature dendritic cells express the inflammatory cytokine in the low level, and thus, even when the cells contact with a T cell, the cells cannot activate a T cell. On the other hand, the mature dendritic cells allow a naive T cell to be activated, and thus, have ability capable of inducing an immune reaction. In order for the immature dendritic cells to be differentiated into the mature dendritic cells, the immature dendritic cells should be exposed to many specific signals to activate a toll-like acceptor. For this reason, many co-stimulatory molecules and proinflammatory cytokine like IL-12 are up-regulated and transferred from tissues to a lymphatic gland, and thus, the projections like fingers, which are the morphological feature of the mature dendritic cells, are appeared.

Meanwhile, in the case where the immature dendritic cells are in different environmental conditions, they may be differentiated into the semi-mature dendritic cells. For example, it may be considered that TNF-α (tumor necrosis factor-α) that releases from the cells during an apoptosis process contributes the differentiation into the semi-mature dendritic cells. The semi-mature dendritic cells become exhibit some of the characteristics of phenotype of the mature dendritic cells after losing some of the characteristics of the immature dendritic cells.

Recently, a study on a therapy for treating cancers or immune-related diseases using the dendritic cells is being performed. For example, Korean Patent Laid-Open Publication No. 10-2010-0109099 discloses the mature dendritic cells for treating a cancer, in which the mature dendritic cells are matured by sensitizing the immature dendritic cells with a cancer-specific antigen protein and Korean Patent No. 10-0524817 discloses the dendritic cells for treating type I diabetes and rheumatoid arthritis, in which the dendritic cells are prepared by treating the immature lymphatic dendritic cells with interferon-gamma. In addition, M. B. Lutz, et al. (J. Exp. Med, 2002, 195(1): 15-21) suggest the experimental results, in which the dendritic cells treated with TNF-α can suppress encephalomyelitis in a C57BL/6 mouse. However, up to now, there are no developments of the tolerogenic dendritic cells having the therapy effect for treating a myocardial infarction.

Therefore, the present inventors studied for developing the tolerogenic dendritic cells for treating cardiac insufficiency that occurs by excessive remodeling of left ventricle in the heart muscle recovery process after an acute myocardial infarction, in which there are no proper therapies for treating the cardiac insufficiency, and as a result, the inventors found that the remodeling of left ventricle is inhibited and the inflammation is alleviated when the tolerogenic dendritic cells are treated to the mouse model with an acute myocardial infarction. Thus, the inventors finally completed the present invention.

SUMMARY

Therefore, an object of the present invention is to provide a method for preparing the tolerogenic dendritic cells for treating a myocardial infarction, in which the method includes culturing the immature dendritic cells in a medium including TNF-α (tumor necrosis factor-α), and serum obtained from an object having a myocardial infarction or the protein extracted from the region of a myocardial infarction of an object having a myocardial infarction.

Another object of the present invention is to provide a pharmaceutical composition for treating a myocardial infarction, including the tolerogenic dendritic cells as an effective component.

In order to achieve the above objects, the present invention provides a method for preparing the tolerogenic dendritic cells for treating a myocardial infarction, in which the method includes culturing the immature dendritic cells in a medium including TNF-α (tumor necrosis factor-α), and serum obtained from an object having a myocardial infarction or the protein extracted from the region of a myocardial infarction of an object having a myocardial infarction.

According to an embodiment of the present invention, the immature dendritic cells may be induced by culturing the cells isolated from the bone marrow of an object having a myocardial infarction.

According to an embodiment of the present invention, the immature dendritic cells may be cultured in the medium including IL-4 (Interleukin-4) and GM-CSF (Granulocyte macrophage colony stimulating factor).

According to an embodiment of the present invention, the protein may be obtained by homogenizing and centrifuging the region of a myocardial infarction isolated from an object having a myocardial infarction.

According to an embodiment of the present invention, the tolerogenic dendritic cells may be prepared by adding 10 to 50 μg/ml of the protein extracted from the region of a myocardial infarction of an object having a myocardial infarction and 1 to 50 ng/ml of TNF-α thereto, and then culturing them.

According to an embodiment of the present invention, the tolerogenic dendritic cells may be prepared by adding 10 to 50 μg/ml of the serum extracted from an object having a myocardial infarction and 1 to 50 ng/ml of TNF-α thereto, and then culturing them.

According to an embodiment of the present invention, for the tolerogenic dendritic cells, the expressions of CD86, CD80, and CD40, which are costimulatory molecules on the cell surface, may be high as compared with the immature dendritic cells, but may be low as compared with the mature dendritic cells.

In addition, the present invention provides a pharmaceutical composition for treating a myocardial infarction, including the tolerogenic dendritic cells as an effective component.

According to an embodiment of the present invention, the composition may exhibit the effects on inhibiting the remodeling of left ventricle and alleviating inflammatory after a myocardial infarction.

According to an embodiment of the present invention, for the tolerogenic dendritic cells, the expressions of CD86, CD80, and CD40, which are costimulatory molecules on the cell surface, may be high as compared with the immature dendritic cells, but may be low as compared with the mature dendritic cells.

According to an embodiment of the present invention, the tolerogenic dendritic cells may be prepared by culturing the immature dendritic cells in the medium including the protein extracted from the region of a myocardial infarction of an object having a myocardial infarction or serum extracted from an object having a myocardial infarction, and TNF-α (tumor necrosis factor-α).

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The heart works by oxygen and nutriment through three cardiovasculars (the coronary arteries), largely. A myocardial infarction means that when any one of three coronary arteries is abruptly blocked due to the fast contraction (twitch) of blood vessel or thrombosis, the supply of oxygen and nutriment into the whole heart or a part of heart is sharply decreased, and thus, the cells or tissues of cardiomyocyte are dead (necrotized).

The present invention relates to a pharmaceutical composition for treating a myocardial infarction as described above, and a method for preparing the composition, and more particularly, to the tolerogenic dendritic cells for treating a myocardial infarction, which can treat cardiac insufficiency that occurs by excessive remodeling of left ventricle in the heart muscle recovery process after an acute myocardial infarction, and a method for preparing the tolergenic dendritic cells.

For the present invention, the term, a "dendritic cell" is a special antigen-presenting cell presenting various antigen samples along with MHC Class I complex or MHC Class II complex to a T cell by absorbing an antigen in cells. The dendritic cells may be divided into the immature dendritic cells, semi-mature dendritic cells, and mature dendritic cells according to the expression level of the surface phenotype or maturity. The expression profile of surface markers of the dendritic cells may be easy through a flow cytometry assay that is known in the art.

For the present invention, the term, "immature dendritic cells," are the dendritic cells, in which the cells are found at the initial mature state of the dendritic cells, CD14 that is a surface phenotype of a mononuclear cell is not expressed, and CD40, CD80, and CD86 that are a co-stimulatory molecule are expressed in a low level.

For the present invention, the term, "mature dendritic cells," means the cells, in which the immature dendritic cells are matured, and then the mature dendritic cells are formed. The mature dendritic cells have ability capable of inducing an immune reaction by increasing the expressions of MHC class II, CD40, CD80, and CD86, releasing a pro-inflammatory cytokine, and then activating a naive T cell.

For the present invention, the term, "semi-mature dendritic cells" means the cells without some of characteristics of the immature dendritic cells and with some of characteristics of the phenotypes of the mature dendritic cells.

The tolerogenic dendritic cells for treating myocardial infarction, which are prepared in the present invention, are characterized of having low expressions of CD86 and CD40 that are co-stimulatory molecules on the cell surface as compared with the mature dendritic cells and high expressions thereof as compared with the immature dendritic cells. Therefore, the tolergenic dendritic cells exhibit similar features with the semi-mature dendritic cells.

For the present invention, the term, "immunologic tolerance" means the state that does not exhibit the immune reaction to a specific antigen. For the present invention, the term, "tolerogenic dendritic cell" means the dendritic cells inducing the tolerance against an autoantigen and inhibiting the proliferation of a T cell, and from the viewpoint of the purpose of the present invention, the tolerogenic dendritic cells of the present invention means the dendritic cells inducing the immunologic tolerance against an autoantigen that generates the excessive inflammatory reaction after a myocardial infarction.

The tolerogenic dendritic cells for treating a myocardial infarction are prepared by a preparing method including culturing the immature dendritic cells in the medium including a protein extract or serum extracted from the heart of the mouse having a myocardial infarction.

In addition, the tolerogenic dendritic cells of the present invention may be obtained by inducing the differentiation of immature dendritic cells. The immature dendritic cells may be directly obtained from bone marrow, spleen, lymph, the thymus, or blood of animals, or may be obtained by culturing the dendritic cell precursors having the immature dendritic cells, for example, pluripotency cells, hematopoietic cells, precursor cells, peripheral-blood mononuclear cells, CD14+ mononuclear cells, or CD34+ mononuclear cells under presence of proper cytokines. The proper cytokines used for obtaining the immature dendritic cells may be the mixture of GM-CSF and IL-4, the mixture of GM-CSF and IL-13, or the mixture of GM-CSF and IL-7, and preferably, the mixture of GM-CSF and IL-4.

The medium capable of being used in the process for differentiating the immature dendritic cells from the dendritic cell precursors derived from bone marrow, spleen, lymph, the thymus, or blood may be any kinds of the general mediums that can be used for culturing animal cells. Preferably, the medium including serum (for example, fetal bovine serum, horse serum, or human serum). Examples of the mediums capable of being used in the present invention may include RPMI series (for example, RPMI 1640), Eagles's MEM (Eagle's minimum essential medium, Eagle), α-MEM, Iscove's MEM, 199 medium, CMRL 1066, F12, F10, DMEM (Dulbecco's modification of Eagle's medium), the mixture of DMEM and F12, Way-mouth's MB752/1, McCoy's 5A, and MCDB series, but the present invention is not limited thereto. These mediums may include other components, for example, antioxidant (for example, β-mercapto ethanol), or antibiotics (for example, penicillin/streptomycin), and the like.

Preferably, the tolerogenic dendritic cells for treating a myocardial infarction according to the present invention may be obtained by isolating the mouse bone marrow-derived cells from the tibia and femur, culturing the cells thus obtained in RPMI 1640 medium including 10% fetal bovine serum, 1% penicillin/streptomycin, rmIL-4, rmG-MCSF, and then treating the protein extract extracted from the heart of mouse having a myocardial infarction at 10 days, and TNF-α to the medium.

The tolerogenic dendritic cells for treating a myocardial infarction, which are prepared according to the method of the present invention, are characterized in that the expressions of CD86 and CD40 that are co-stimulatory molecules on the cell surface are low as compared with the mature dendritic cells and high as compared with the immature denderitic cells. The expression profile of the surface markers may be easy through a flow cytometry assay that is known in the art.

In addition, the tolerogenic dendritic cells for treating a myocardial infarction, which are prepared by the method of the present invention, are characterized of having a specific therapeutic effect on the cardiac insufficiency generated after a myocardial infarction, specifically, an acute myocardial infarction. In an specific embodiment of the present invention, in order to confirm the therapeutic effect of the tolerogenic dendritic cells prepared in the present invention on a myocardial infarction, the tolerogenic dendritic cells are injected twice to the mouse model with a myocardial infarction, the mouse is sacrificed, and then the degree of inflammation is confirmed by an immunohistochemistry staining and the naked eye. As a result, it can be confirmed that while the inflammation is entirely spread on the control group, the inflammation reaction is reduced in the case of injecting the dendritic cells of the present invention, and specifically, in the case of injecting $1 \times 10^6$ cells, the inflammation is significantly reduced. Therefore, it can be found that the dendritic cells of the present invention have excellent effect on treating the cardiac insufficiency generated after a myocardial infarction.

Therefore, the tolerogenic dendritic cells of the present invention may be provided as an effective component for the composition for treating a myocardial infarction.

In the present invention, the composition for treating a myocardial infarction may further include a proper carrier, excipient, and diluent that are generally used for preparing a pharmaceutical composition in addition to the tolerogenic dendritic cells, and may be formulated in a type of an oral formulation such as powders, granules, tablets, capsule, suspension, emulsion, syrup, and aerosol, externals, suppository, or sterile injection solutions according to a general method, and then used.

The composition may be formulated by using diluents or excipients such as filler, a bulking agent, a binding agent, a wetting agent, a disintegrating agent, and a surfactant, that are generally used in the case of formulating the composition. A solid formulation for an oral administration may be tablets, pellets, granules, capsules, and the like, and such a solid formulation may include at least one of excipients and/or lubricants. A liquid formulation for an oral administration may be suspension, internal solution, an emulsion, syrups, and the like, and in addition to water and liquid paraffin that are simple diluents, various excipients, for example, a wetting agent, a sweetening agent, a flavoring agent, a preserved agent, and the like may be included. The formulation for a parenteral administration may be a sterile aqueous solution, nonaqueous solvent, suspension, an emulsion, a freeze drying formulation, suppository, and the like.

The administration amount of the composition may be different in the condition and weight of a patient, the degree of disease, a type of drug, a route of administration, and a period of administrate, but may be properly selected by a person who skilled in the art. For obtaining more preferred effects, the administration amount of the composition of the present invention may be 0.1 mg/kg to 100 mg/kg per a day with respect to an effective component, but the present invention is not limited thereto. The administration may be performed one time a day, or several times. The composition of the present invention may be administrated in various routes to animals, preferably, mammals including human. All kinds of the administration routes may be expected, for example, oral, intravenous, muscle, subcutaneous injection, and the like.

Hereinafter, the present invention will be described in detail with reference to Examples. The advantages, features, and method for achieving them for the present invention will be obvious with reference to Examples to be described. However, these Examples are only for explaining the present invention in detail, but the range of the present invention is not limited to Examples.

Example 1

Preparation of Mouse Model Having Acute Myocardial Infarction

For the present invention, 5-week C57BL/6 mice (male) were purchased from Central Lab. Animal Inc. (Korea), and bred in a cage which is under an feeding environment, such as the temperature of 23° C., the humidity of 55%, the illumination of 300 to 500 lux, and the period of light and shade for 12 hours. As the feed, PURINA RODENT LABORATORY CHOW 5001™ (Purina Mills, USA) was purchased, and freely supplied, and as drinking water, distilled water was supplied for the animals to freely drink. After an acclimation process for 2 weeks, the intubation was performed by using 22 G angio needle for anesthetized mice, the hairs on the chest of mice were removed, the skin was cut, the ribs were slightly opened, and then pericardium in the heart was removed. Since then, the left anterior descending artery of coronary artery was completely ligated by slightly lifting it with nylon silk. Since then, the air was deflated from the lung of mouse, and the surgical site was sutured.

Figure 1:
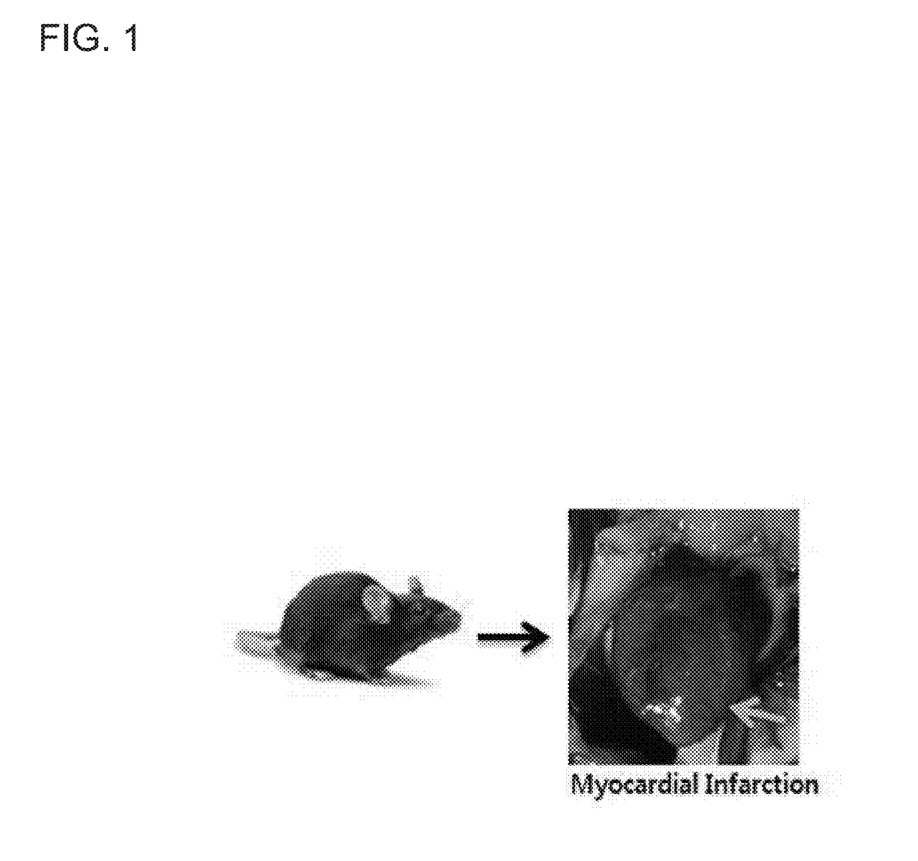
FIG. 1 is a photograph illustrating the region of a myocardial infarction of mouse model having a myocardial infarction prepared in Example 1.

As a result, as illustrated in FIG. 1, it could be confirmed that a myocardial infarction was exhibited in a white color in the lower section of the heart (apex) of the mouse model prepared.

Example 2

Preparations of Heart Protein Extract and Serum from Mice Models Having Myocardial Infarction for Preparing Tolerogenic Dendritic Cells for Treating Myocardial Infarction In order to prepare the tolerogenic dendritic cells for treating a myocardial infarction, after preparing the mice models having a myocardial infarction in <Example 1> for 24 hours, the mice models were sacrificed, and then the region of myocardial infarction of the heart was obtained. The obtained heart was clearly washed with PBS, added into a MACS M tube with PBS, and then homogenized in a gentle MACS dissociator. The homogenized PBS including the heart was centrifuged at 2,000 rpm and 4° C. for 10 minutes, and then the supernatant was collected. The collected supernatant was centrifuged at 13,000 rpm and 4° C. for 10 minutes in order to remove the remained tissues from the obtained protein solution, and then filtered with 0.2 μm syringe filter in order to treat the cells, and 5 μg/ml of the protein was quantified with a Bradford method.

In addition, the serum for preparing the tolerogenic dendritic cells for treating a myocardial infarction was prepared by collecting the whole blood at 24 hours after preparing the mouse model preparation, centrifuging the whole blood at 3,000 rpm and 10 minutes, and then collecting the supernatant.

Example 3

Preparation of Tolerogenic Dendritic Cells for Treating Myocardial Infarction

The mouse bone marrow-derived cells were isolated from the tibia and femur, and then cultured in a RPMI 1640 medium including 10% fetal bovine serum, 1% penicillin/streptomycin, rmIL-4 (2 ng/ml) and rmGM-CSF (20 ng/ml) to start the culture of the dendritic cells. At 3 days, 6 days, and 6 days after culturing, the same medium was changed, and at 10 days, LPS (lipopolysaccharide, 1 μg/ml) and the protein extract extracted from the heart of mouse having a myocardial infarction were treated to obtain the mature dendritic cells (mDCs). At 10 days, the protein extract (25 μg/ml) extracted from the heart of mouse having a myocardial infarction or serum (25 μg/ml) extracted from an object having a myocardial infarction, and TNF-α (10 ng/ml) were treated to obtain the tolerogenic dendritic cells. The immature dendritic cells were obtained by changing the medium for the same times without treating the protein extract. For each of the dendritic cells, the size, granular, and surface phenotype of dendritic cell were confirmed through a flow cytometer.

Figure 2A:
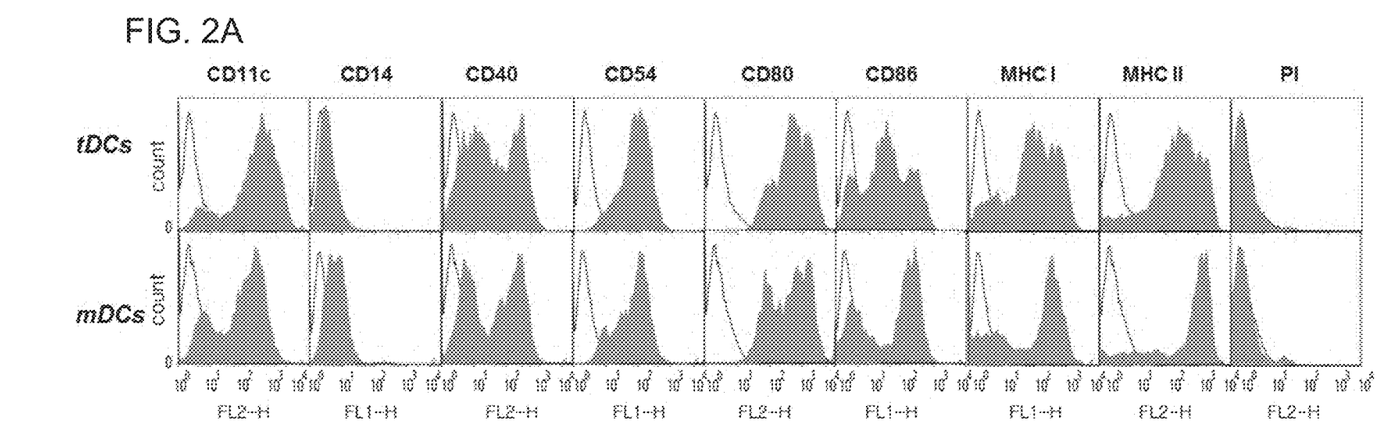
FIGS. 2A and 2B show the results of the cell surface phenotypes of the immature dendritic cells (Immature DC), the tolerogenic DC, and mature DC that are prepared in Example 3 and are confirmed by a flow cytometry assay.
Figure 2B:
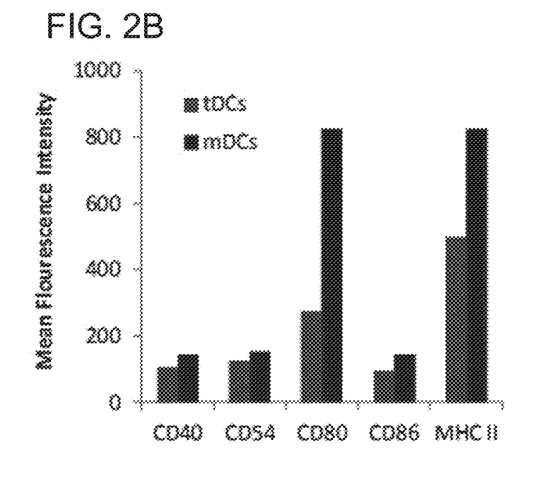

As a result, it could be confirmed that for the mouse bone marrow-derived cells, the expression of CD11c was gradually increased by treating the protein extract extracted from the heart of mouse having a myocardial infarction, and at 9 days of the culture, 80% or more thereof was expressed. In addition, it could be confirmed that for the mouse bone marrow-derived cells, the expression amounts of CD86, CD80, and CD40 that are co-stimulatory molecules were continuously increased, and at 9 days of the culture, the features of the dendritic cells were exhibited. Meanwhile, it could be confirmed that the expression of CD14 that was a surface phenotype of monocyte was disappeared from 6 days, at 8 and 9 days, the dendritic cells were differentiated into the immature denderitic cells, and at 9 days, the dendritic cells were subjected to a maturing process into the tolergenic and mature dendritic cells. Therefore, the present inventors could prepare the tolerogenic dendritic cells having high values of CD86, CD80, and CD40 that are co-stimulatory molecules as compared with the immature dendritic cells and low values thereof as compared with the mature dendritic cells (see FIG. 2)

Example 4

Confirmation of Treg Cell Expression of Tolerogenic Dendritic Cells

In order to confirm the effect of the tolerogenic dendritic cells derived from the serum of the mouse having a myocardial infarction and protein extract extracted from the heart of mouse having a myocardial infarction on inhibiting the inflammation, the immature dendritic cells (imDCs), the tolerogenic dendritic cells (tDCs) cultured by treating the extract or serum as described above thereto, and the mature dendritic cells (mDCs) were mixed with a T cell in a ratio of 1:10, respectively, and then cultured for 72 hours. The Foxp3 induction ability of the T cell was confirmed by using a flow cytometer.

Figure 3A:
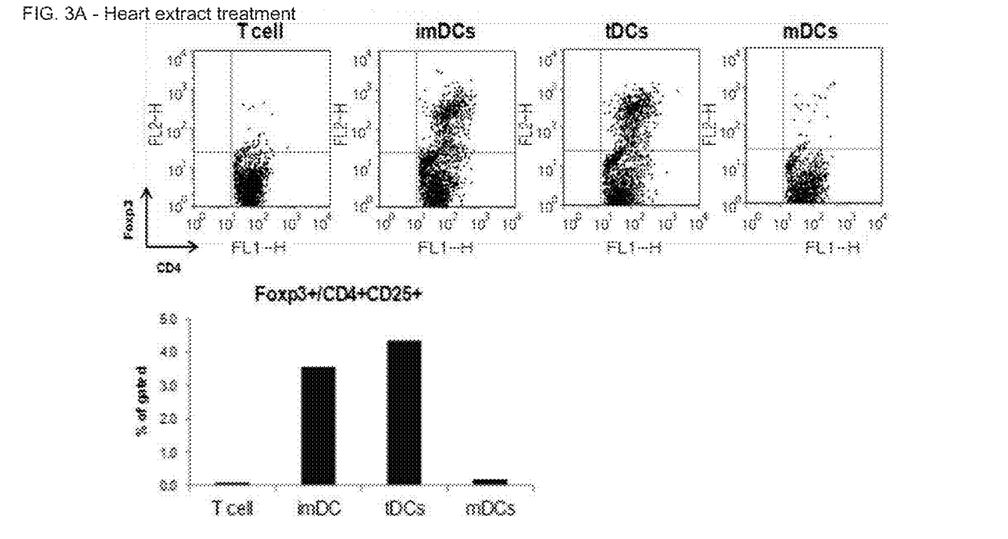
FIGS. 3A and 3B show the results of a flow cytometry assay illustrating Foxp3+ expression induction effect of a T cell after co-culturing a T cell and the tolerogenic dendritic cells prepared by treating with a protein extract or serum of the mouse model having a myocardial infarction thereto.
Figure 3B:
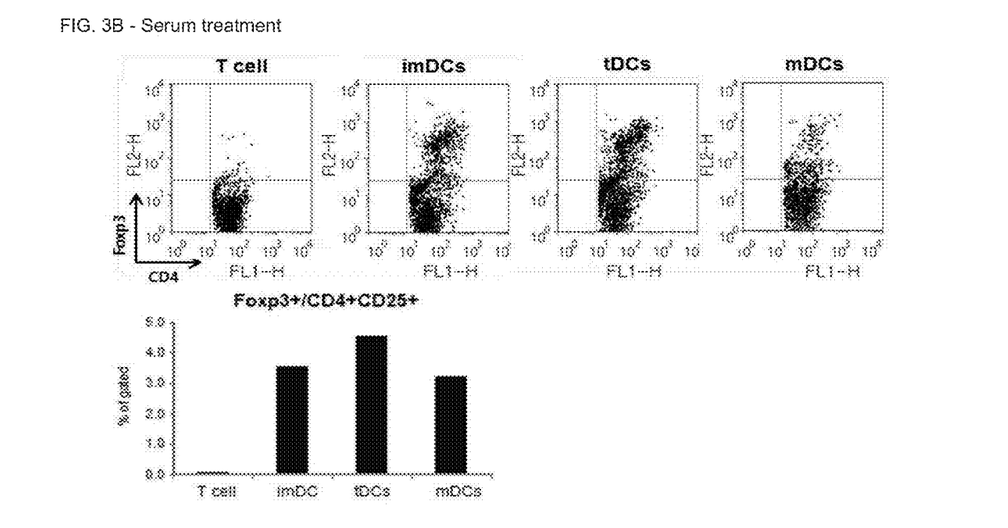

As a result, it could be confirmed that the tolerogenic dendritic cells (tDCs) obtained by treating the protein extract extracted from the heart of mouse having a myocardial infarction or the serum of mouse having a myocardial infarction allow the expression of Foxp3+ by a T cell to increase maximally (see FIG. 3).

Example 5

Effect of Tolerogenic Dendritic Cells on Inhibiting Remodeling of Left Ventricle after Myocardial Infarction of Mouse Model According to Treatment of Tolerogenic Dendritic Cells The left ventricle was remodeled during the recovery process of heart muscle after a myocardial infarction. The excessive remodeling (adverse remodeling) of left ventricle may be one of the biggest causes for generating the cardiac insufficiency after a myocardial infarction. In other words, this is because when a myocardial infarction occurs, the remodeling is performed at the infarct region and also noninfarct region, and thus, left ventricle is expanded and the heart muscle of left ventricle is thinned, thereby reducing the contractile force and developing cardiac insufficiency. One of the biggest causes for exhibiting the excessive remodeling of left ventricle after a myocardial infarction is a lack of vascularization and the inflammatory reaction that is excessively activated after a myocardial infarction.

Figure 4:
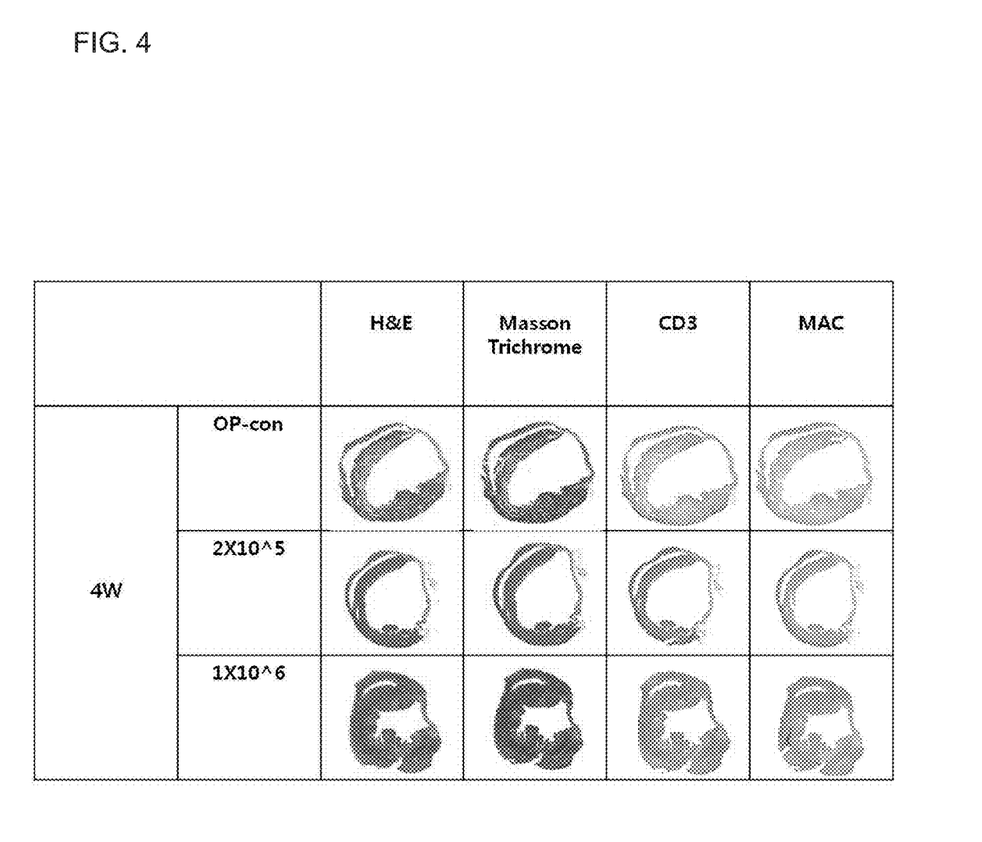
FIG. 4 is a result of observing the inhibition of the remodeling of left ventricle and inflammatory alleviation effect after injecting the tolerogenic dendritic cells according to the present invention to the mouse model having a myocardial infarction.
Figure 5:
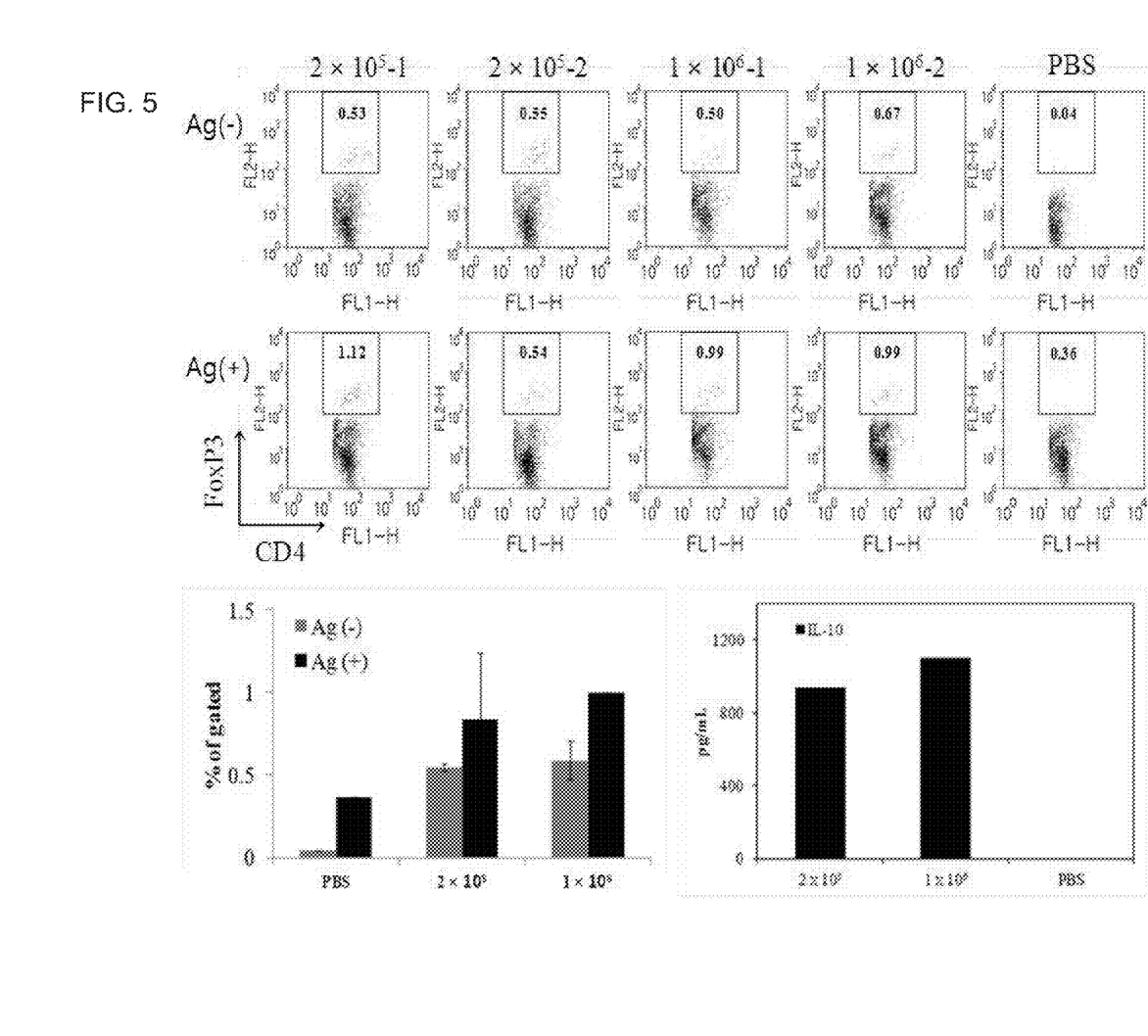
FIG. 5 is a result of assaying the expression amount of Foxp3+ and IL-10 after injecting the tolerogenic dendritic cells according to the present invention to the mouse model having a myocardial infarction, which are confirmed through a flow cytometry assay.

Therefore, the present inventors observed whether or not the effect of the tolerogenic dendritic cells on inhibiting the remodeling of left ventricle after a myocardial infarction was exhibited after administrating the tolerogenic dendritic cells prepared in <Example 3> using the mouse model having a myocardial infarction of <Example 1>. To achieve this, the present inventors performed the subcutaneous injections of $2\times10^5$ cells of the tolerogenic dendritic cells prepared in <Example 3> after 24 hours of the mousse model preparation per a mouse and $1\times10^6$ cells thereof for a mouse (first injection), and after 1 week, performed the subcutaneous injections of the same cell numbers of the tolerogenic dendritic cells to the above mouse model (second injection). After 4 weeks, the mice were sacrificed, the bloods were extracted, and then the spleens and hearts were isolated to observe the degree of the myocardial infarction. In other words, the central part of the heart was cut after scarifying the mouse, prepared in a paraffin block, and then the thickness of 5 μm was cut to prepare a tissue fraction. For a morphological observation, H&E staining was performed; for measuring the degree of fibrosis, the masson trichome was performed; for confirming the degree of the inflammatory reaction, the immunochemical staining was performed by treating CD3 and MAC (macrophage) antibody. As a result, it could be confirmed that as compared with the control group being only treated with PBS, the remodeling of heart muscle was significantly decreased, the fibrosis of heart muscle was decreased, and the inflammatory reaction was significantly inhibited, when being morphological-observed in the group treated with $1\times10^6$ of the tolerogenic dendritic cells (see FIG. 4).

Example 6

Estimation of Immune Reaction in Mouse Model According to Treatment of Tolerogenic Dendritic Cells From <Example 5>, it could be confirmed that the remodeling of heart muscle was inhibited in the mouse model having a myocardial infarction, which was treated with the tolerogenic dendritic cells. Therefore, the present inventors studied the mechanism therefor.

To achieve this, as described in <Example 5>, for the control group being only treated with PBS and the experimental groups being subjected to the subcutaneous injections of $2\times10^5$ cell/a mouse and $1\times10^6$ cell/a mouse of the tolerogenic dendritic cells, the mice were sacrificed at 4 weeks after the second injection, respectively, and the spleens were extracted and ground to analysis the expression amount of Foxp3 of T cells using a flow cytometer and measure the expression amount of IL-10 that is a anti-inflammatory cytokine (Th2 cytokine) with ELISA.

As a result, it could be confirmed that for the experimental group injected with $1\times10^6$ cells, the expression amount of Foxp3+ controlling T cell was highest and also the expression amount of IL-10 was high.

Example 7

Observation of In Vivo Trafficking Image after Labeling Tolerogenic Dendritic Cells with Li-Cor NIR Meanwhile, the present inventors expected that the tolerogenic dendritic cells were moved into the surrounding lymphatic gland, and then induced the immune reaction, and thereby observed their movement by injecting the tolerogenic dendritic cells to the hypodermis of the groin region that was easily observed.

To achieve this, $2\times10^7$ cell of the tolerogenic dendritic cells prepared in Example 3, which did not include serum, were floated in 1 ml of Diluent C included in CellVue Burgundy Fluorescent Cell Labeling Kit (Li-Cor, eBioscience Inc, CA.). After adding $4\times10^{-6}$M CellVue Dye thereto, 1 ml of Diluent C was further added thereto. After diluting the Dye well through a pipetting, the tube was shaken for 2 to 5 minutes. After mixing the Dye, the cell viability was confirmed, and then by treating 2 ml of serum thereto, the reaction was stopped for 1 minute. The reaction solution was centrifuged at 25° C. and 100×g for 10 minutes to remove the supernatant completely, and then, washed 2 to 3 times with a complete media to remove the remained dye completely. After completing the washing, the cells were diluted to confirm the cell biability and count the number of the cells. The cells were diluted to be $1\times10^7$/ml, was subcutaneously injected to the thigh of the mouse, and immediately after the injection, the injection site of the mouse was confirmed through an IMPULSE apparatus (PEARL IMPULSE (small animal imaging system) (Li-Cor)). The trafficking of the cells injected for 48 hours were performed.

Figure 6:
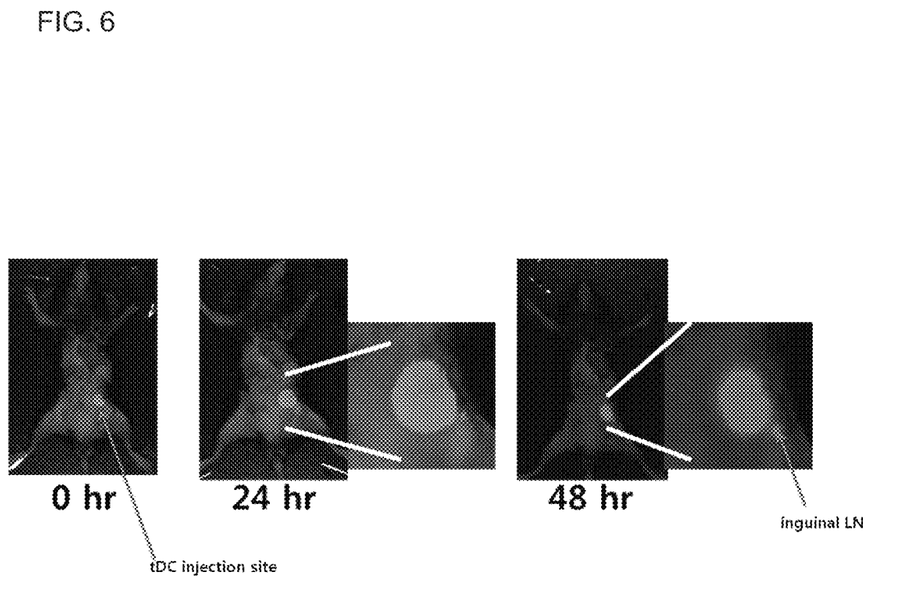
FIG. 6 is a result of confirming in vivo trafficking image after injecting the tolerogenic dendritic cells according to the present invention that are subjected to Li-cor NIR labeling to the mouse model having a myocardial infarction.

As a result, as illustrated in FIG. 6, it could be confirmed that the tolerogenic dendritic cells according to the present invention were moved only into the inguinal lymph node that was the lymph node being very adjacent to the subcutaneous injection site. Therefore, it could be confirmed that the tolerogenic dendritic cells moved into the inguinal lymph node induce the immune reaction in the lymph node.

Example 8

Confirmation of Effect on Treating Mouse Model Having Myocardial Infarction According to the Treatment of Tolerogenic Dendritic Cells Using MRI The present inventors subcutaneously injected $1\times10^6$ cells of the tolerogenic dendritic cells prepared within 24 hours using the method of <Example 3> to the thigh of the mouse model having a myocardial infarction of <Example 1>, and then, after 1 week, secondarily injected the same number of the cells using the same method. At 28 days after the first injection, MRI was performed. After putting the mouse under anesthesia using an anesthesia ventilator, the tail vein was fixed, and then the image was taken before injecting a contrast medium. Since then, the concentration of 0.3 mmol/kg of gadolinium was injected to the tail vein, and then, T1 weight image was taken in the unit of 10 minutes for 30 minutes after the injection to obtain the images.

Figure 7:
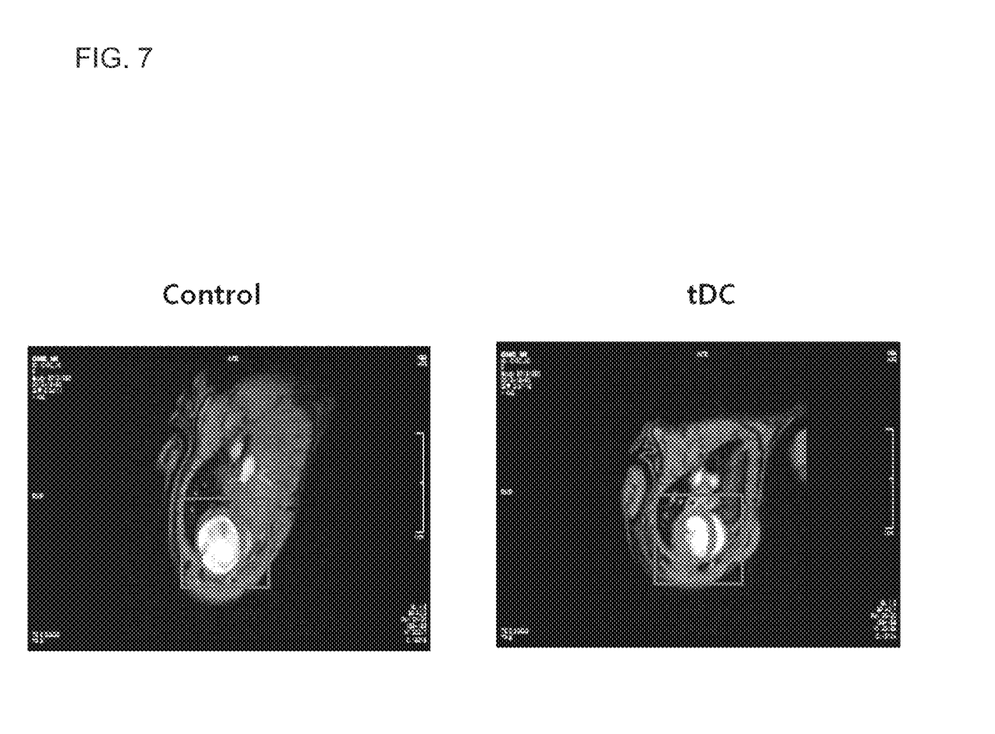
FIG. 7 is a MRI result obtained after injecting the tolerogenic dendritic cells according to the present invention to the mouse model having a myocardial model.

As a result, it could be confirmed that at 24 hours after the operation, as compared with the control group being treated with PBS, in the case of treating the tolerogenic dendritic cells, the left ventricle was greatly widened and the wall of the left ventricle was also very thinned (see FIG. 7).

From Examples as described above, the present inventors found that the protein and serum extracted from the region of myocardial infarction of the mouse model having a myocardial infarction have the ability capable of inducing the tolerogenic dendritic cells, and when the tolerogenic dendritic cells induced as described above are treated to the mouse model having a myocardial infarction, the remodeling of left ventricle that may be generated after a myocardial infarction can be inhibited and the attack rate of cardiac insufficiency can be significantly reduced. Therefore, the present inventors can confirm the effect on treating a myocardial infarction according to the present invention.

According to the present invention, by providing a pharmaceutical composition for treating a myocardial infarction, including the tolerogenic dendritic cells as an effective component, and a method for preparing the tolerogenic dendritic cells for treating a myocardial infarction, the excessive remodeling of the heart muscle and inflammatory reaction can be inhibited in the heart muscle recovery process after an acute myocardial infarction, and thus, the incidence rate of cardiac insufficiency can be significantly reduced. Therefore, the present invention can be effectively used for treating a myocardial infarction.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of inhibiting remodeling of left ventricle after myocardial infarction comprising:
   (i) preparing a pharmaceutical composition comprising tolerogenic dendritic cells for treating a myocardial infarction, the method comprising culturing immature dendritic cells in a medium including TNF-α (tumor necrosis factor-α), and protein extracted from a region of a myocardial infarction of an object having a myocardial infarction or serum obtained from an object having a myocardial infarction; and
   (ii) administering the pharmaceutical composition according to (i) comprising tolerogenic dendritic cells as an effective component to a subject in need thereof, wherein the tolerogenic dendritic cells have high expression amounts of CD86, CD80, and CD40 that are co-stimulatory molecules on a cell surface as compared with immature dendritic cells and low expression amount of CD86, CD80, and CD40 as compared with mature dendritic cells, wherein the tolerogenic dendritic cells express CD11c, but do not express CD14; and wherein the tolerogenic dendritic cells have high expression amounts of Foxp3+ as compared with mature dendritic cells and immature dendritic cells.

2. The method according to claim 1, wherein the composition has an effect on alleviating the inflammation and inhibiting the remodeling of left ventricle after a myocardial infarction.

* * * * *